United States Patent
Samejima et al.

(10) Patent No.: US 10,327,696 B2
(45) Date of Patent: Jun. 25, 2019

(54) ACTION NOTIFICATION SYSTEM, EXERCISE INFORMATION MEASUREMENT APPARATUS, ELECTRONIC DEVICE, ACTION NOTIFICATION METHOD, AND ACTION NOTIFICATION PROGRAM

(71) Applicant: OMRON HEALTHCARE CO., LTD., Muko-shi, Kyoto (JP)

(72) Inventors: Mitsuru Samejima, Kyoto (JP); Takehiro Hamaguchi, Kyoto (JP); Naoki Takeishi, Kyoto (JP); Nobuki Yakura, Kyoto (JP); Shinichi Toda, Kyoto (JP); Kengo Nishiyama, Kyoto (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 0 days.

(21) Appl. No.: 15/862,664

(22) Filed: Jan. 5, 2018

(65) Prior Publication Data

US 2019/0008449 A1 Jan. 10, 2019

Related U.S. Application Data

(63) Continuation of application No. PCT/JP2016/064481, filed on May 16, 2016.

(30) Foreign Application Priority Data

Jul. 6, 2015 (JP) .................. 2015-135341

(51) Int. Cl.
*A63B 24/00* (2006.01)
*A61B 5/00* (2006.01)
*A61B 5/11* (2006.01)

(52) U.S. Cl.
CPC ............ *A61B 5/486* (2013.01); *A61B 5/0022* (2013.01); *A61B 5/1118* (2013.01); *A61B 5/742* (2013.01);
(Continued)

(58) Field of Classification Search
CPC ..... A61B 5/486; A61B 5/1118; A61B 5/0022; A61B 5/7405; A61B 5/742; A61B 5/7455;
(Continued)

(56) References Cited

U.S. PATENT DOCUMENTS

| 7,028,547 B2* | 4/2006 | Shiratori ............... A61B 5/1118 702/141 |
| 7,742,894 B2* | 6/2010 | Chen .................... A61B 5/1038 340/573.1 |

(Continued)

FOREIGN PATENT DOCUMENTS

| DE | 11 2011 102 379 T5 | 8/2013 |
| JP | 2008-73456 A | 4/2008 |

(Continued)

OTHER PUBLICATIONS

Official Communication issued in International Patent Application No. PCT/JP2016/064481, dated Aug. 9, 2016.

*Primary Examiner* — Hung T Nguyen
(74) *Attorney, Agent, or Firm* — Keating and Bennett, LLP

(57) ABSTRACT

An action notification system includes an exercise information measurement apparatus that includes an action determiner to determine an action of a user based on a detection signal of a body motion sensor, and a transmission controller to cause a communicator to transmit characteristic information of a detection signal waveform of the body motion sensor, which corresponds to the determined action, and an (Continued)

exercise information measurement apparatus that includes a characteristic information acquirer to acquire the characteristic information transmitted from the exercise information measurement apparatus via a communicator, and an output device controller to cause a vibrator to operate in accordance with the acquired characteristic information.

13 Claims, 6 Drawing Sheets

(52) U.S. Cl.
CPC .......... *A61B 5/7405* (2013.01); *A61B 5/7455* (2013.01); *A63B 24/0062* (2013.01); *A61B 2562/0219* (2013.01)

(58) Field of Classification Search
CPC . A63B 24/0062; A63B 24/00; A63B 71/0622; G06F 19/3481; G01C 21/20; G08B 21/24
USPC ..... 340/539.1, 539.11, 539.12, 573.1, 573.4; 600/300, 301; 700/91
See application file for complete search history.

(56) References Cited

U.S. PATENT DOCUMENTS

| 7,867,141 | B2 * | 1/2011 | Matsumura | ........... A61B 5/1118 |
| | | | | 377/24.2 |
| 2003/0208335 | A1 | 11/2003 | Unuma et al. | |
| 2008/0076978 | A1 | 3/2008 | Ouchi et al. | |
| 2012/0116719 | A1 | 5/2012 | Takahashi et al. | |
| 2012/0283855 | A1 * | 11/2012 | Hoffman | ................ G01C 21/20 |
| | | | | 700/91 |
| 2013/0123959 | A1 | 5/2013 | Kan et al. | |
| 2013/0182092 | A1 | 7/2013 | Ishii et al. | |
| 2015/0042475 | A1 * | 2/2015 | White | .................... G16H 20/30 |
| | | | | 340/573.1 |

FOREIGN PATENT DOCUMENTS

| JP | 2009-125270 A | 6/2009 |
| JP | 2011-90426 A | 5/2011 |
| JP | 2012-71004 A | 4/2012 |
| JP | 2012-199663 A | 10/2012 |
| WO | 2007/082389 A1 | 7/2007 |

\* cited by examiner

ACTION NOTIFICATION SYSTEM, EXERCISE INFORMATION MEASUREMENT APPARATUS, ELECTRONIC DEVICE, ACTION NOTIFICATION METHOD, AND ACTION NOTIFICATION PROGRAM

CROSS REFERENCE TO RELATED APPLICATIONS

This application claims the benefit of priority to Japanese Patent Application No. 2015-135341 filed on Jul. 6, 2015 and is a Continuation Application of PCT Application No. PCT/JP2016/064481 filed on May 16, 2016. The entire contents of each application are hereby incorporated herein by reference.

BACKGROUND OF THE INVENTION

1. Field of the Invention

The present invention relates to an action notification system, an exercise information measurement apparatus, an electronic device, an action notification method, and an action notification program.

2. Description of the Related Art

In recent years, an exercise information measurement apparatus that can measure exercise information including an activity amount (information indicating the amount of activity of a person, such as a step count, a walking distance, or calories expended), or a movement speed (a movement distance per unit time, or the amount of time it takes to move a unit distance) by using a body motion sensor that detects movement of a body, such as an acceleration sensor or an angular velocity sensor, has been actively developed.

An exercise information measurement apparatus that has a communication function is known as this kind of exercise information measurement apparatus, and various services can be provided by using the communication function.

For example, JP 2011-090426A discloses a pedometer that directly exchanges the activity intensity, which is information that relies on the walking pitch, with another pedometer, and determines walking compatibility by comparing the activity intensities.

Although not related to an exercise information measurement apparatus, JP 2012-199663A discloses an information communication terminal that includes an inertia sensor, an acceleration sensor, and a sensor to detect bodily information such as body temperature and heartbeat, and performs wireless communication, the information communication terminal starting communication with another information communication terminal as a result of an event that occurs in response to a sensor detection state.

According to JP 2012-199663A, when no event occurs, the other information communication terminal, which functions as a slave, enters a state of low power consumption compared to a waiting state, and therefore an information communication system with low power consumption can be constructed.

Also, although not related to an exercise information measurement apparatus, JP 2008-073456A discloses a bodily information measurement apparatus that achieves lower power consumption by transmitting bodily information to an external device at a suitable time.

According to JP 2011-090426A, it is possible to provide a new service to the user by using the exercise information of multiple users. In the future, it will be necessary to provide various applications that use exercise information measured by an exercise information measurement apparatus, so as to promote use of the exercise information measurement apparatus. In particular, an application that improves communication between users of the exercise information measurement apparatuses as in JP 2011-090426A is thought to be effective.

JP 2012-199663A and JP 2008-073456A merely disclose communication control methods for saving power, and no consideration is given to providing a service intended to connect people.

SUMMARY OF THE INVENTION

Preferred embodiments of the present invention provide action notification systems and action notification methods according to which it is possible to deepen a connection between people, and exercise information measurement apparatuses, electronic devices, and non-transitory computer-readable media containing action notification programs that can be used in the action notification systems.

An action notification system according to a preferred embodiment of the present invention includes: an exercise information measurement apparatus including a first body motion sensor that detects body motion of a user, a first exercise information calculator that calculates exercise information based on a detection signal of the first body motion sensor, a first communicator that communicates with an external device, an action determiner that determines an action of the user based on the detection signal of the first body motion sensor, and a transmission controller that causes the first communicator to transmit characteristic information of a detection signal waveform of the first body motion sensor, which corresponds to the action determined by the action determiner; and an electronic device including a second communicator that communicates with an external device, an output device including a vibrator, a speaker, or a light emitter, a characteristic information acquirer that acquires the characteristic information transmitted from the exercise information measurement apparatus via the second communicator, and an output device controller that causes the output device to operate in accordance with the characteristic information acquired by the characteristic information acquirer.

An exercise information measurement apparatus according to a preferred embodiment of the present invention includes: a body motion sensor that detects body motion of a user; an exercise information calculator that calculates exercise information based on the detection signal of the body motion sensor; a communicator that communicates with an external apparatus; an action determiner that determines an action of the user based on the detection signal of the body motion sensor; and a transmission controller that causes the communicator to transmit characteristic information of a detection signal waveform of the body motion sensor, which corresponds to the action determined by the action determiner, to an electronic device, wherein the electronic device includes an output device including a vibrator, a speaker, or a light emitter, and an output device controller that causes the output device to operate in accordance with the characteristic information.

An electronic device according to a preferred embodiment of the present invention includes: a first communicator that communicates with an external apparatus; an output device including a vibrator, a speaker, or the like; a characteristic information acquirer that acquires, via the first communicator, characteristic information of a detection signal waveform of a first body motion sensor, the characteristic information having been transmitted from an exercise information measurement apparatus including a first body motion sensor that detects body motion of a user, a first exercise information calculator that calculates exercise information based on a detection signal of the first body motion sensor, a second communicator that communicates with an external device, an action determiner that determines an action of the user based on the detection signal of the first body motion sensor, and a transmission controller that causes the second communicator to transmit the characteristic information, which corresponds to the action determined by the action determiner; and an output device controller that causes the output device to operate in accordance with the characteristic information acquired by the characteristic information acquirer.

An action notification method according to a preferred embodiment of the present invention includes: an action determination step in which an exercise information measurement apparatus including a body motion sensor that detects body motion of a user, an exercise information calculator that calculates exercise information based on a detection signal of the body motion sensor, and a first communicator that communicates with an external device determines an action of the user based on the detection signal of the body motion sensor; a transmission step in which, from the first communicator, the exercise information measurement apparatus transmits characteristic information of a detection signal waveform of the body motion sensor, which corresponds to the action determined in the action determination step; a characteristic information acquisition step in which an electronic device including a second communicator that communicates with an external device and an output device including a vibrator, a speaker, or a light emitter acquires the characteristic information transmitted in the transmission step via the second communicator; and an output device control step in which the electronic device causes the output device to operate in accordance with the characteristic information acquired in the characteristic information acquisition step.

A non-transitory computer readable medium according to a preferred embodiment of the present invention includes stored thereon an action notification program that is an action notification program that causes a processor of an exercise information measurement apparatus, which includes a body motion sensor that detects body motion of a user, an exercise information calculator that calculates exercise information based on a detection signal of the body motion sensor, and a first communicator that communicates with an external device, to execute: an action determination step of determining an action of the user based on the detection signal of the body motion sensor; and a transmission control step of causing the first communicator to transmit the exercise information measurement apparatus transmits characteristic information of a detection signal waveform of the body motion sensor, which corresponds to the action determined in the action determination step, to an electronic device, wherein the electronic device includes a second communicator that communicates with an external apparatus, an output device including a vibrator, a speaker, or a light emitting element, a characteristic information acquirer that acquires the characteristic information transmitted in the transmission control step, and an output device controller that causes the output device to operate in accordance with the acquired characteristic information.

A non-transitory computer readable medium according to a preferred embodiment of the present invention includes stored thereon an action notification program that is an action notification program that causes a processor of an electronic device, which includes a first communicator that communicates with an external device and an output device including a vibrator, a speaker, or a light emitting element, to execute: a characteristic information acquisition step of acquiring, via the first communicator, characteristic information of a detection signal waveform of a first body motion sensor, the characteristic information having been transmitted from an exercise information measurement apparatus including the first body motion sensor that detects body motion of a user, a first exercise information calculator that calculates exercise information based on a detection signal of the first body motion sensor, a second communicator that communicates with an external device, an action determiner that determines an action of the user based on the detection signal of the first body motion sensor, and a transmission controller that causes the second communicator to transmit the characteristic information, which corresponds to the action determined by the action determiner; and an output device control step of causing the output device to operate in accordance with the characteristic information acquired in the characteristic information acquisition step.

According to preferred embodiments of the present invention, it is possible to provide action notification systems and action notification methods according to which it is possible to deepen a connection between people, and exercise information measurement apparatuses, electronic devices, and non-transitory computer-readable media containing action notification programs that can be used in the action notification systems.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described with reference to the drawings.

Figure 1:
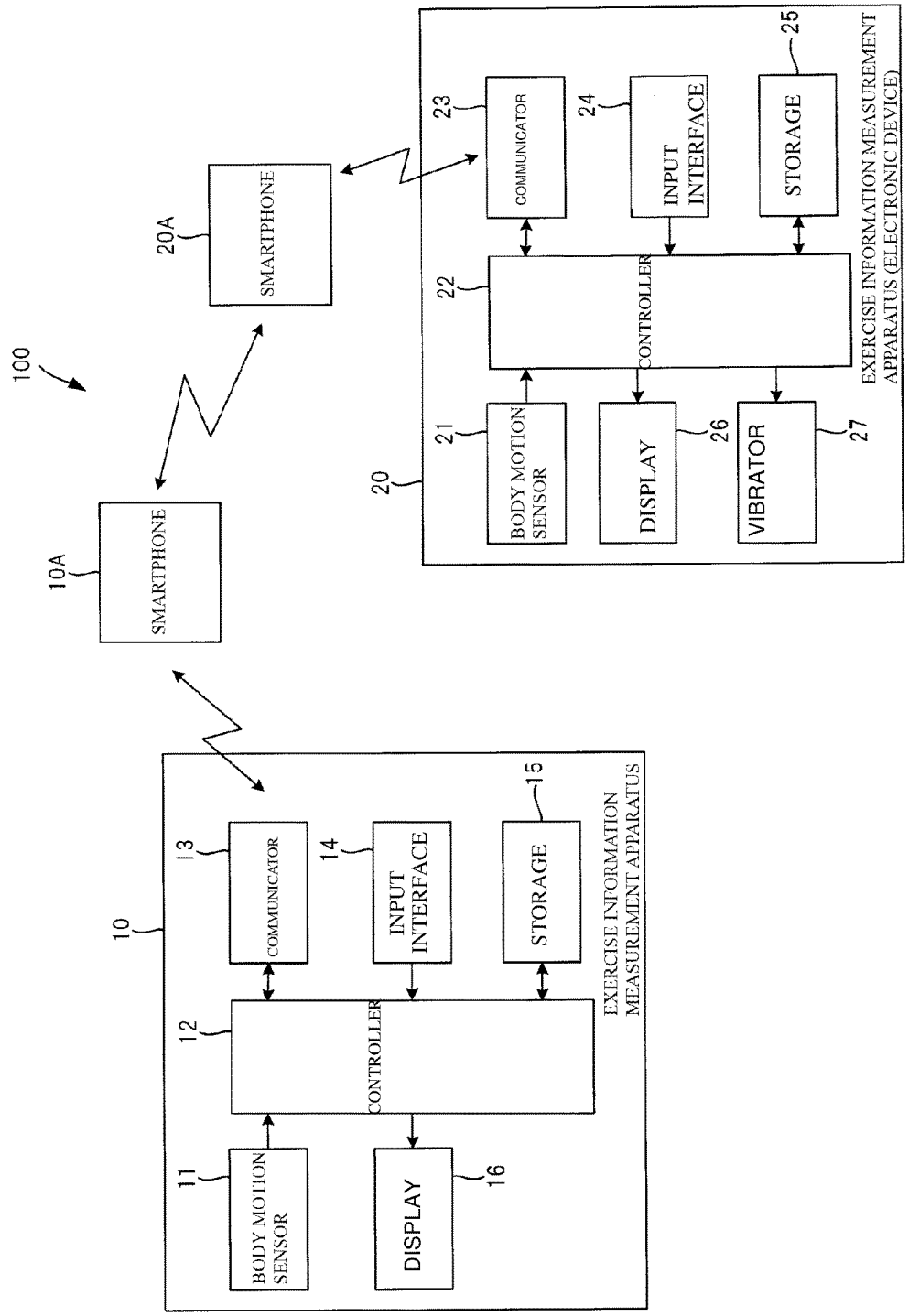
FIG. 1 is a diagram showing a schematic configuration of an action notification system 100 for describing a preferred embodiment of the present invention.

FIG. 1 is a diagram showing a schematic configuration of an action notification system 100 for describing a preferred embodiment of the present invention.

The action notification system 100 includes an exercise information measurement apparatus 10, a smartphone 10A, a smartphone 20A, and an exercise information measurement apparatus 20 defining and functioning as an electronic device.

The exercise information measurement apparatus 10 and the exercise information measurement apparatus 20 are used while worn (includes a state of being inserted in a pocket of an article of clothing or a bag owned by a user) on the body of a user, and pedometers, activity amount meters, sports watches, and the like are examples thereof.

The exercise information measurement apparatus 10 is worn by a user A (not shown) and the smartphone 10A is owned by the user A.

The exercise information measurement apparatus 20 is worn by a user B (not shown) and the smartphone 20A is owned by the user B.

The exercise information measurement apparatus 10 includes a body motion sensor 11, a controller 12 that performs overall control, a communicator 13, an input interface 14, a display 16 that displays various types of information, and a storage 15 including a storage medium such as a flash memory or a ROM (Read Only Memory) and a driver that controls reading and writing of data in the storage medium.

The body motion sensor 11 detects the body motion of the user A wearing the exercise information measurement apparatus 10. An acceleration sensor or angular velocity sensor is used as the body motion sensor 11. Hereinafter, description will be given assuming that the body motion sensor 11 is a triaxial acceleration sensor, for example.

The controller 12 preferably includes a processor that executes a program stored on the ROM of the storage 15, for example.

The communicator 13 is an interface that performs near-field wireless communication with an external device including the smartphone 10A.

Near-field wireless communication refers to communication that conforms to a communication standard according to which communication can be performed directly between devices without use of a network such as the Internet.

A communication interface conforming to ANT, a communication interface conforming to Bluetooth (registered trademark), a communication interface conforming to BLE (Bluetooth Low Energy), a communication interface conforming to ZigBee, a communication interface conforming to Wi-Fi, or the like preferably is used as the interface, for example.

The input interface 14 is a device that inputs various instructions to the controller 12, and may preferably include buttons or a touch panel mounted on the display 16, for example.

The storage 15 stores a detection signal waveform (an xyz triaxial composite acceleration waveform) of the body motion sensor 11 and stores information needed for the operation of the exercise information measurement apparatus 10.

The exercise information measurement apparatus 20 includes a body motion sensor 21, a controller 22 that performs overall control, a communicator 23, an input interface 24, a display 26 that displays various types of information, a storage 25 including a storage medium such as a flash memory or a ROM and a driver that controls reading and writing of data in the storage medium, and a vibrator 27 that includes a vibration element and a driving circuit that drives the vibration element.

The body motion sensor 21 detects the body motion of the user B wearing the exercise information measurement apparatus 20. An acceleration sensor or angular velocity sensor is used as the body motion sensor 21.

The controller 22 preferably includes a processor that executes a program stored on the ROM of the storage 25, for example.

The communicator 23 is an interface that performs near-field wireless communication with an external device including the smartphone 20A.

The input interface 24 is a device that inputs various instructions to the controller 22, and may preferably include buttons or a touch panel mounted on the display 26, for example.

The storage 25 stores a detection signal detected by the body motion sensor 21 and stores information needed for the operation of the exercise information measurement apparatus 20.

The vibrator 27 vibrates the entirety of the exercise information measurement apparatus 20 by vibrating a vibration element based on an instruction from the controller 22 and performs notification to the user B of the exercise information measurement apparatus 20.

With the action notification system 100, a predetermined application program (hereinafter referred to as an "app") is installed by the users on the smartphone 10A and the smartphone 20A.

This app has a function of managing exercise information measured by a paired exercise information measurement apparatus and a function of enabling the action of the user of the paired exercise information measurement apparatus to be transmitted to a user of another exercise information measurement apparatus.

Specifically, with this app, the user of the smartphone 10A can register a device (here, the smartphone 20A owned by the user B) of a person to whom the user's actions are to be transmitted.

With this app, the smartphone 10A transfers predetermined data received through near-field wireless communication from the exercise information measurement apparatus 10 paired with the smartphone 10A to the registered smartphone 20A. Communication between smartphones is performed via a mobile telephone network.

With the smartphone 20A, when data transmitted from the smartphone 10A is received through an installed app, the received data is transmitted to the exercise information measurement apparatus 20 paired with the smartphone 20A through near-field wireless communication.

With the action notification system 100, predetermined data is transmitted from the exercise information measurement apparatus 10 to the exercise information measurement apparatus 20 through this series of processes.

Figure 2:
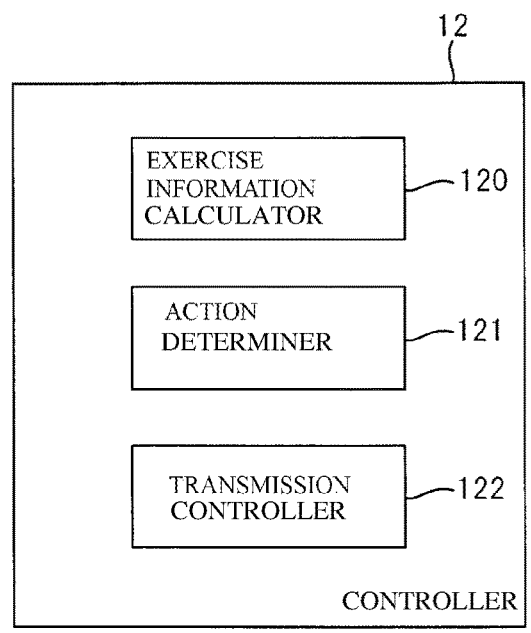
FIG. 2 is a diagram showing functional blocks realized by a controller 12 due to a program stored in a storage 15 of an exercise information measurement apparatus 10 shown in FIG. 1 being executed by a processor.

FIG. 2 is a diagram showing functional blocks realized by the controller 12 due to an action notification program stored in the storage 15 of the exercise information measurement apparatus 10 shown in FIG. 1 being executed by a processor.

As shown in FIG. 2, the controller 12 includes an exercise information calculator 120, an action determiner 121, and a transmission controller 122.

Based on the detection signal of the body motion sensor 11, the exercise information calculator 120 calculates exercise information including at least one of an activity amount, such as the step count, the movement distance, or expended calories of the user of the exercise information measurement apparatus 10, and a movement speed, using a known method.

The exercise information calculator 120 extracts the detection signal waveform with a sampling period of 1 Hz, for example, from the detection signal of the body motion sensor 11, temporarily stores it in the storage 15, and calculates the exercise information using the temporarily-stored detection signal waveform.

The action determiner 121 determines the action of the user based on the detection signal of the body motion sensor 11.

Figure 3:
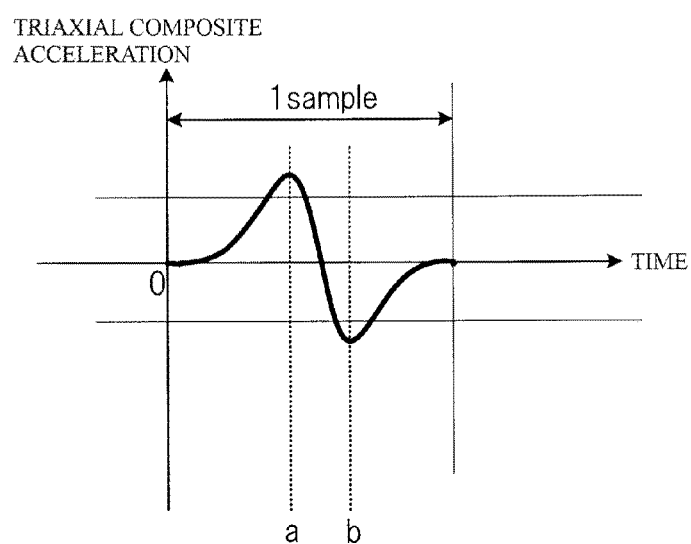
FIG. 3 is a diagram showing an example of a waveform of composite acceleration of a triaxial acceleration output from a body motion sensor 11.

FIG. 3 is a diagram showing an example of a waveform of a composite acceleration of a triaxial acceleration output from a body motion sensor 11. FIG. 3 shows a waveform of a sample obtained by cutting a waveform at a sampling interval of 1 Hz, the waveform having been obtained when the user A transitioned from a sitting state to a standing state (action=standing up), or when the user A transitioned from a standing state to a sitting state (action=sitting down).

Figure 4:
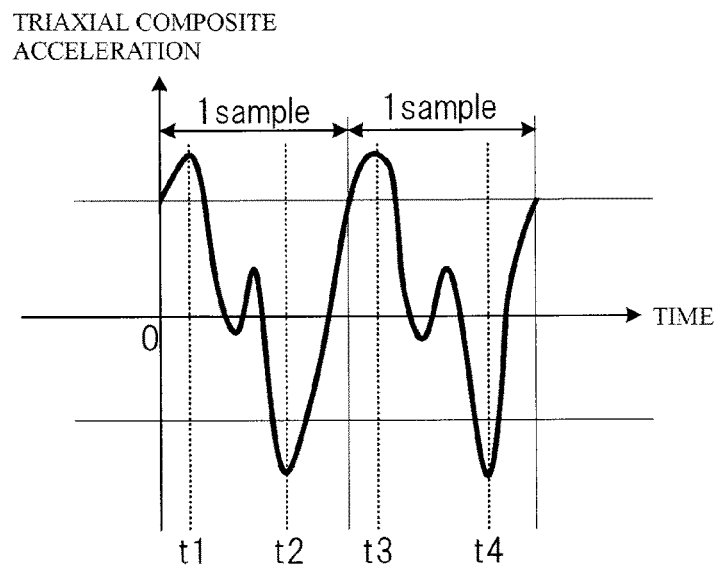
FIG. 4 is a diagram showing another example of a waveform of composite acceleration of a triaxial acceleration output from the body motion sensor 11.

FIG. 4 is a diagram showing another example of a waveform of a composite acceleration of a triaxial acceleration output from a body motion sensor 11. FIG. 4 shows a waveform of two samples obtained by cutting a waveform at a sampling interval of 1 Hz, the waveform having been obtained when the user A was walking or running.

The action determiner 121 determines actions corresponding to waveforms such as those shown in FIGS. 3 and 4 by matching the waveforms with predetermined waveform patterns for each action.

The action determiner 121 periodically (e.g., every 20 seconds) performs processing to determine an action based on the detection signal waveform of the body motion sensor 11 and stores the action determined through that processing and the detection signal waveform used in the action determination in a storage medium of the storage 15 in association with a time.

The action determiner 121 determines the action that was determined the most often through multiple instances of the above-described processing in a predetermined period (e.g., 5 minutes) determined in advance, as the action in the predetermined period of the user A.

In each predetermined period, the transmission controller 122 causes the smartphone 10A to transmit characteristic information of the detection signal waveform of the body motion sensor 11 corresponding to the action in the predetermined period determined by the action determiner 121 from the communicator 13.

The characteristic information is transmitted to the exercise information measurement apparatus 20 via the smartphone 10A and the smartphone 20A.

The characteristic information of the detection signal waveform corresponding to a certain action is information that indicates the amplitude value at a characteristic point (point of inflection) of a waveform pattern determined as that certain action, and the detection time of the characteristic point.

For example, the detection signal waveform in FIG. 3, which corresponds to the action of "standing up", has a maximum amplitude value at a time a, and has a minimum amplitude value at a time b.

The characteristic information of the detection signal waveform of one sample corresponding to the action shown in FIG. 3 (standing up) includes the amplitude value at the time a, the amplitude value at the time b, and the interval information for the time a and the time b.

Also, the detection signal waveform in FIG. 4, which corresponds to the action of the user walking has a maximum amplitude value at a time t1 and a minimum amplitude value at a time t2 in the first sample. In the second sample, the detection signal waveform has a maximum amplitude value at a time t3 and a minimum amplitude value at a time t4.

The characteristic information of the detection signal waveform of two samples, which corresponds to the action shown in FIG. 4 (walking), includes the amplitude value at the time t1, the amplitude value at the time t2, the amplitude value at the time t3, the amplitude value at the time t4, the interval information for the time t1 and the time t2, the interval information for the time t2 and the time t3, and the interval information for the time t3 and the time t4.

Figure 5:
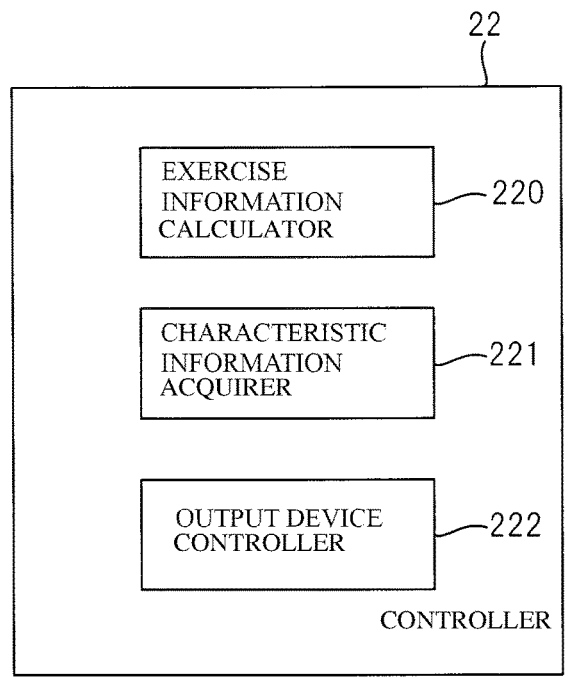
FIG. 5 is a diagram showing functional blocks realized by a controller 22 due to a program stored in a storage 25 of an exercise information measurement apparatus 20 shown in FIG. 1 being executed by a processor.

FIG. 5 is a diagram showing functional blocks realized by the controller 22 due to a program stored in the storage 25 of the exercise information measurement apparatus 20 shown in FIG. 1 being executed by a processor.

As shown in FIG. 5, the controller 22 includes an exercise information calculator 220, a characteristic information acquirer 221, and an output device controller 222.

Based on the detection signal of the body motion sensor 21, the exercise information calculator 220 calculates exercise information including at least one of an activity amount, such as the step count, the movement distance, or expended calories of the user of the exercise information measurement apparatus 20, and a movement speed, using a known method.

The characteristic information acquirer 221 acquires the characteristic information transmitted from the exercise information measurement apparatus 10 via the communicator 23.

The output device controller 222 generates an amplitude pattern to cause the vibrator 27 to vibrate based on the characteristic information acquired by the characteristic information acquirer 221 and causes the vibrator 27 defining and functioning as the output device to operate in accordance with the pattern.

Specifically, the output device controller 222 generates a pattern with a predetermined period in which the vibrator 27 is vibrated, in accordance with the interval between the maximum value and the minimum value of the amplitude of the detection signal waveform included in the characteristic information.

Figure 6:
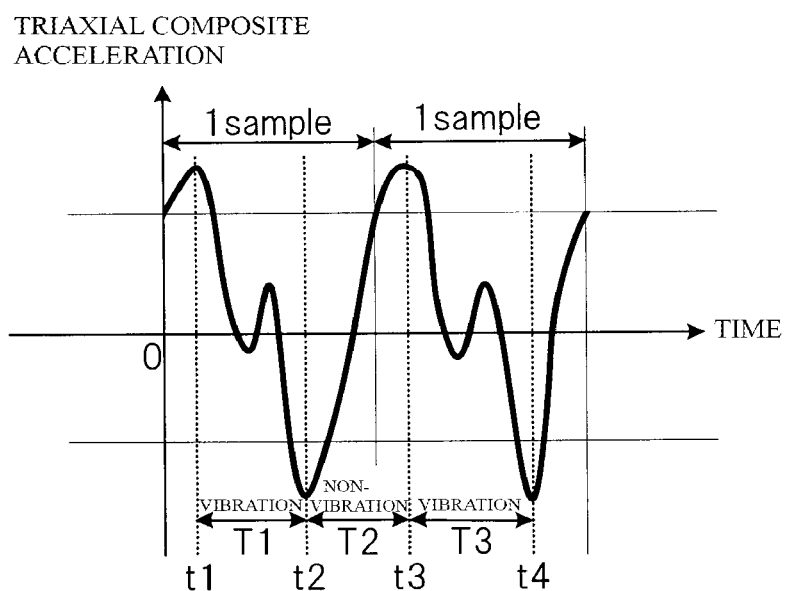
FIG. 6 is a diagram for describing an example of generating a vibration pattern of a vibrator 27 according to the exercise information measurement apparatus 20 shown in FIG. 1.

FIG. 6 is a diagram for describing an amplitude pattern generated by the output device controller 222.

As described above, the characteristic information of the detection signal waveform shown in FIG. 4 includes information on an interval T1 for the time t1 and the time t2, an interval T2 for the time t2 and the time t3, and an interval T3 for the time t3 and the time t4.

Based on the characteristic information, the output device controller 222 generates a pattern in which the vibrator 27 is vibrated for the interval T1, then the vibrator 27 is stopped for the interval T2, and then the vibrator 27 is vibrated for the interval T3.

When the vibrator 27 operates according to this pattern, the exercise information measurement apparatus 20 vibrates for the interval T1, does not vibrate for the interval T2, and finally, vibrates for the interval T3.

If the characteristic information acquired by the controller 22 is the characteristic information of the detection signal waveform shown in FIG. 3, the output device controller 222 generates a pattern in which the vibrator 27 is vibrated for the amount of time of the interval for the time a and the time b.

Thus, the vibration pattern of the vibrator 27 is created in accordance with the detection signal waveform of the body motion sensor 11 of the exercise information measurement apparatus 10. For this reason, if the user A of the exercise information measurement apparatus 10 performs an action of "standing up", the exercise information measurement apparatus 20 vibrates in response to that action, and thus it is possible to tell the user B of the exercise information measurement apparatus 20 that the user A stood up.

Also, when the user A of the exercise information measurement apparatus 10 performs an action of "walking", the exercise information measurement apparatus 20 changes from vibrating, to non-vibrating, to vibrating in response to the action, and thus it is possible to tell the user B of the exercise information measurement apparatus 20 that the user A is moving.

Note that if the user A of the exercise information measurement apparatus 10 is running, the intervals T1 to T3 in FIG. 6 last a shorter amount of time compared to when the user A is walking. For this reason, if the action of the user A is "running", the exercise information measurement apparatus 20 operates by transitioning at a high speed between vibrating, not vibrating, and vibrating. Accordingly, the user B can know whether the user A is walking or running according to the speed of vibration change.

Figure 7:
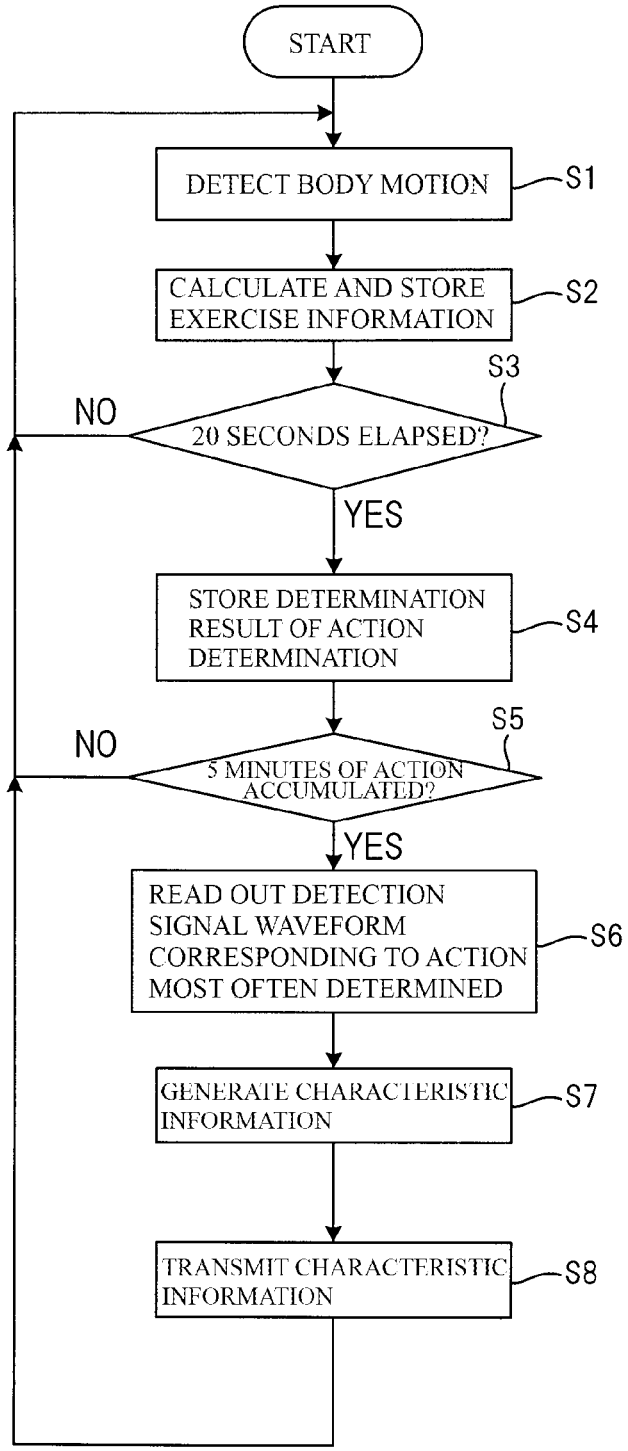
FIG. 7 is a flowchart for describing an operation of the exercise information measurement apparatus 10 of the action notification system 100 shown in FIG. 1.

FIG. 7 is a flowchart for describing an operation of the exercise information measurement apparatus 10 of the action notification system 100 shown in FIG. 1. The exercise information measurement apparatus 10 can set the action notification mode of notifying another person of the action of the user, and FIG. 7 shows operations of the exercise information measurement apparatus 10 for which the action notification mode has been set.

After the action notification mode is set, the controller 12 of the exercise information measurement apparatus 10 resets the count time of an internal timer and starts counting. Also, the body motion of the user A is detected by the body motion sensor 11 of the exercise information measurement apparatus 10 (step S1).

The exercise information calculator 120 of the controller 12 of the exercise information measurement apparatus 10 calculates the exercise information based on the detection signal of the body motion sensor 11 detected in step S1 and stores it in the storage 15 (step S2).

The processing of step S1 and step S2 is repeated until 20 seconds elapses from the action notification mode setting, in accordance with the internal timer of the controller 12.

When 20 seconds elapses from the action notification mode setting (step S3: YES), the action determiner 121 of the controller 12 acquires the newest detection signal waveform sampled from the detection signal of the body motion sensor 11 and determines the action at the current time of the user A based on the detection signal waveform. The action determiner 121 stores the determined action type and the detection signal waveform used in the determination in association with each other in the storage 15 (step S4).

After step S4, the action determiner 121 determines whether or not five minutes' worth of action determination results were stored in the storage 15 (step S5).

If the result of the determination in step S5 is NO, the controller 2 resets the count time of the internal timer and the processing returns to step S1.

If the result of the determination in step S5 is YES, the action determiner 121 specifies the most common action type among the five minutes' worth of action determination results (15 instances of action types determined every 20 seconds) stored in the storage 15, and determines the specified action type as the action of the user A of the most recent five-minute period.

Also, the action determiner 121 acquires the sampling signal waveform corresponding to the determined action from the storage 15 (step S6) and generates the characteristic information of the acquired sampling signal waveform (step S7).

If the determined action is "standing up" or "sitting down", the action determiner 121 acquires one sampling signal waveform that is illustrated in FIG. 3 and is used in determining the action, from the storage 15.

If the determined action is "walking" or "running", the action determiner 121 acquires two sampling signal waveforms that are illustrated in FIG. 4 and are used in determining the action, from the storage 15.

Next, the transmission controller 122 of the controller 12 transmits the characteristic information generated in step S7 and the ID information of the exercise information measurement apparatus 10 from the communicator 13 to the smartphone 10A (step S8).

After step S8, the controller 12 erases the five minutes' worth of action determination results stored in the storage 15, resets the count time of the internal timer, and returns the processing to step S1.

Upon receiving the characteristic information and the ID information transmitted from the communicator 13 in step S8, the smartphone 10A transmits the characteristic information and the ID information to the pre-registered smartphone 20A using the function of an app. Then, the smartphone 20A transmits the received characteristic information and ID information to the exercise information measurement apparatus 20 using the function of an app.

Figure 8:
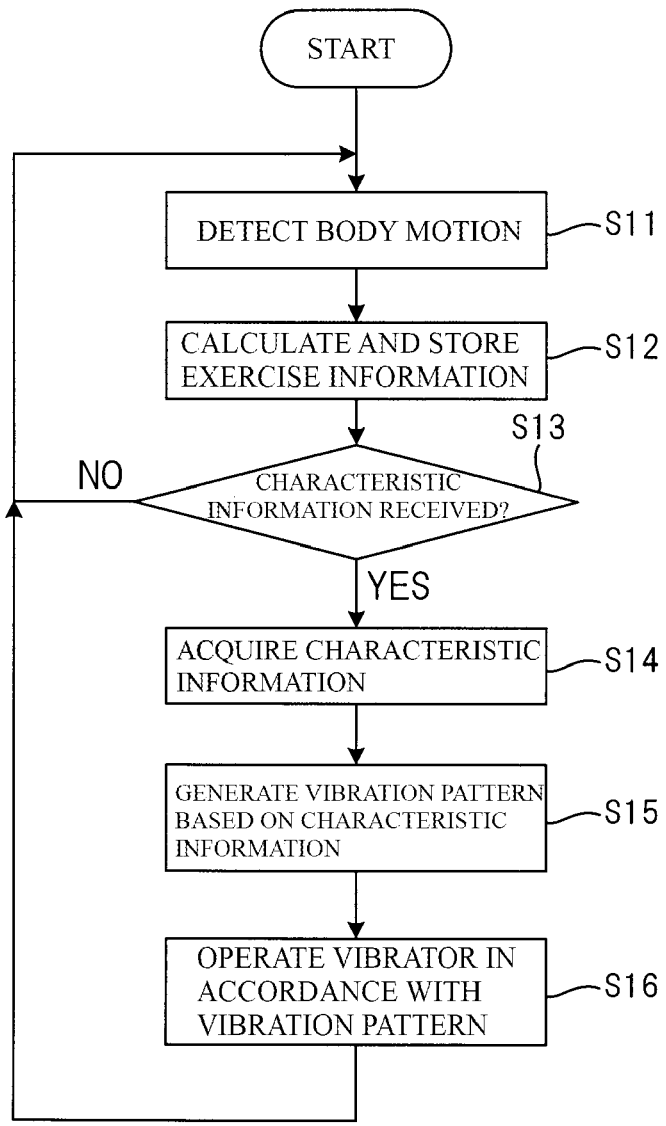
FIG. 8 is a flowchart for describing an operation of the exercise information measurement apparatus 20 of the action notification system 100 shown in FIG. 1.

FIG. 8 is a flowchart for describing an operation of the exercise information measurement apparatus 20 of the action notification system 100 shown in FIG. 1.

When body motion is detected by the body motion sensor 21 in step S11, the exercise information calculator 220 of the controller 22 of the exercise information measurement apparatus 20 calculates the exercise information based on the detection signal and stores it in the storage 25 (step S12).

The characteristic information acquirer 221 of the controller 22 determines whether or not the characteristic information and the ID information were received from the smartphone 20A through the communicator 23 (step S13).

When the result of the determination in step S13 is YES, the characteristic information acquirer 221 acquires the received characteristic information and ID information (step S14). When the result of the determination in step S13 is NO, the processing returns to step S11.

After step S14, the output device controller 222 of the controller 22 generates information of the vibration pattern based on the characteristic information acquired by the characteristic information acquirer 221 (step S15) and causes the vibrator 27 to vibrate in accordance with the generated information (step S16). At this time, the controller 22 may display information indicating that vibration is occurring in accordance with the action of the user A on the display 26, in accordance with the acquired ID information.

After step S16, the controller 22 returns the processing to step S11.

As described above, according to the action notification system 100, the exercise information measurement apparatus 20 vibrates with a vibration pattern corresponding to the action of the user A of the exercise information measurement apparatus 10. For this reason, the user A can tell the user B the action of the user A.

Thus, even if the user A and the user B are at separate locations, the user B can feel the action of the user A through the skin, and for example, use as a communication tool between romantic partners or family members is possible. The action notification system 100 can also be used to watch over the elderly or children.

Also, according to the action notification system 100, the vibration pattern of the vibrator 27 is determined in the exercise information measurement apparatus 20 based on the characteristic information of the detection signal waveform of the body motion sensor 11 of the exercise information measurement apparatus 10.

For this reason, it is possible to tell the user B of the exercise information measurement apparatus 20 the action of the user A of the exercise information measurement apparatus 10 in real time, and thus completeness required of a communication tool is increased.

Also, according to the action notification system 100, the characteristic information is generated in each predetermined period (every five minutes in the example shown in FIG. 7) and is transmitted to the exercise information measurement apparatus 20. With the exercise information measurement apparatus 20, in each predetermined period, vibration occurs with a pattern corresponding to the action of the user A.

Thus, with the exercise information measurement apparatus 20, vibration is not performed constantly in response to the action of the user A, and therefore the user B is able to feel the action of the user A without feeling any annoyance. Also, the battery life of the exercise information measurement apparatus 20 is improved.

The action notification system 100 can be modified as follows, for example.

First Modified Example

The exercise information measurement apparatus 20 may be an electronic device that does not include the body motion sensor 21 and the exercise information calculator 220 (e.g., a dedicated device sold in a set with the exercise information measurement apparatus 10).

Alternatively, the smartphone 20A may include a constituent element other than the body motion sensor 21 and the exercise information calculator 220 of the exercise information measurement apparatus 20 and may have a system configuration obtained by removing the exercise information measurement apparatus 20.

According to the action notification system 100 of FIG. 1, the exercise information measurement apparatus 10 and the exercise information measurement apparatus 20 are needed, and therefore an increase in the number of apparatuses sold can be expected by the manufacturer of the exercise information measurement apparatus. Also, since the user A and the user B actively use the exercise information measurement apparatuses, it is possible to promote use of the apparatuses, which contributes to advancing the health of the users.

Second Modified Example

With the action notification system 100, the smartphone 10A transmitted the characteristic information received from the exercise information measurement apparatus 10 to the exercise information measurement apparatus 20 via the smartphone 20A using the function of an app.

With the second modified example, when the transmission destination of the characteristic information (the smartphone 20A paired with the exercise information measurement apparatus 10) is registered in the smartphone 10A, the smartphone 10A transmits the transmission destination information to the exercise information measurement apparatus 10. Then, the transmission controller 122 of the exercise information measurement apparatus 10 transmits the generated characteristic information, instruction information instructing transmission of the characteristic information to the transmission destination designated by the transmission destination information, and the ID information of the exercise information measurement apparatus 10 to the smartphone 10A.

With the smartphone 10A, the characteristic information, instruction information, and ID information are transmitted to the smartphone 20A in accordance with the instruction information. With the smartphone 20A, the characteristic information, instruction information, and ID information are transmitted to the exercise information measurement apparatus 20 in accordance with the instruction information. Thus, it is possible to instruct the transmission destination of the characteristic information and the like using the exercise information measurement apparatus 10 instead of the smartphone 10A.

Third Modified Example

The characteristic information and the like may be transmitted and received directly by the exercise information measurement apparatus 10 and the exercise information measurement apparatus 20 without using the smartphones 10A and 20A. Also, communicators that can connect to a mobile telephone network may be used as the communicators 13 and 23, and transmission and reception of the characteristic information and the like may be performed by the exercise information measurement apparatus 10 and the exercise information measurement apparatus 20 via the mobile telephone network.

According to this modified example, even a user who does not have a smartphone can use the service, and a promotion of use of the service or an increase in sales of the exercise information measurement apparatus can be expected.

Fourth Modified Example

The transmission controller 122 of the exercise information measurement apparatus 10 may use the detection signal waveform of the body motion sensor 11 corresponding to the action in the predetermined period determined by the action determiner 121 as the characteristic information. In other words, the sampling waveform illustrated in FIG. 3 or 4 is generated as the characteristic information.

In this case, the output device controller 222 of the exercise information measurement apparatus 20 obtains the interval for the time a and the time b in FIG. 3 based on the acquired characteristic information and causes the vibrator 27 to operate such that the interval becomes a vibration period.

Alternatively, the output device controller 222 obtains the intervals T1, T2, and T3 in FIG. 4 from the acquired characteristic information and causes the vibrator 27 to operate such that the intervals T1 and T3 become vibration periods and the interval T2 becomes a non-vibration period.

As with the action notification system 100, if the signal waveform itself is not used as the characteristic information, the data communication amount is reduced, and therefore it is possible to reduce the power consumption of the exercise information measurement apparatus 10.

Fifth Modified Example

A speaker may be used instead of the vibrator 27 of the exercise information measurement apparatus 20. In this case, the output device controller 222 generates a sound pattern based on the characteristic information and the sound is output from the speakers in accordance with the pattern.

For example, in FIG. 6, the output device controller 222 performs control to output the sound in the period T1, to not output the sound in the period T2, and to output the sound in the period T3. Accordingly, the user B is able to feel the action of the user A according to changes in the sound.

Sixth Modified Example

A light emitter including a light emitting element such as an LED or an organic EL element, and a driver that drives the light emitting element may be used instead of the vibrator 27 of the exercise information measurement apparatus 20. In this case, the output device controller 222 generates a light emission pattern based on the characteristic information and the light emitter emits the light in accordance with the light emission pattern.

For example, in FIG. 6, the output device controller 222 performs control to cause the light emitter to emit light in the period T1, cause the light emitter to extinguish the light in the period T2, and cause the light emitter to emit light in the period T3. Accordingly, the user B is able to feel the action of the user A according to changes in the light.

Seventh Modified Example

A known smartphone includes all hardware except for the controller 12 of the exercise information measurement apparatus 10 or all hardware except for the controller 22 of the exercise information measurement apparatus 20.

Accordingly, an action can be notified to users by causing a processor of a known smartphone to function as the controller 12 or the controller 22 according to an application program that can be downloaded via a network, for example.

In this case, since communication between smartphones can be performed without using the communicator 13 and the communicator 23, the communicator 13 and the communicator 23 are not essential in the smartphone.

According to this modified example, development of a new apparatus is not necessary, and it is possible to provide a service at a low cost.

Preferred embodiments of the present invention and modifications thereto can be provided by storing a program that causes a computer to execute the steps of the flowchart shown in FIG. 7 or FIG. 8, or a program that causes a computer to function as the functional blocks shown in FIG. 2 or FIG. 5, stored in a computer-readable non-transitory storage medium.

This kind of "computer-readable storage medium" includes, for example, an optical medium such as a CD-ROM (Compact Disc-ROM), a magnetic storage medium such as a memory card, and the like. Also, this kind of program can be provided through downloading via a network.

The preferred embodiments and modifications disclosed herein are meant to be in all ways exemplary and not limiting. The scope of the present invention is indicated not by the above description but by the claims and is intended to encompass all equivalent meanings of the claims and all modifications within the scope.

As described above, the following items are disclosed in the present specification.

In one of the preferred embodiments of the present invention disclosed herein, an action notification system includes: an exercise information measurement apparatus including a first body motion sensor that detects body motion of a user, a first exercise information calculator that calculates exercise information based on a detection signal of the first body motion sensor, a first communicator that communicates with an external device, an action determiner that determines an action of the user based on the detection signal of the first body motion sensor, and a transmission controller that causes the first communicator to transmit characteristic information of a detection signal waveform of the first body motion sensor, which corresponds to the action determined by the action determiner; and an electronic device including a second communicator that communicates with an external device, an output device including a vibrator, a speaker, or a light emitter, a characteristic information acquirer that acquires the characteristic information transmitted from the exercise information measurement apparatus via the second communicator, and an output device controller that causes the output device to operate in accordance with the characteristic information acquired by the characteristic information acquirer.

In one of the preferred embodiments of the action notification system of the present invention disclosed herein, the first body motion sensor is a triaxial acceleration sensor, the characteristic information includes information indicating an interval between a time at which an amplitude of a portion corresponding to the action in a triaxial composite acceleration waveform, which is the detection signal waveform of the triaxial acceleration sensor, reaches its maximum, and a time at which the amplitude reaches its minimum, and in accordance with the interval, the output device controller determines a period of causing the vibrator to vibrate, a period of causing the speaker to output sound, or a period of causing the light emitter to emit light.

In one of the preferred embodiments of the action notification system of the present invention disclosed herein, the action determiner periodically performs processing to determine an action of the user based on the detection signal of the first body motion sensor and determine an action that was most often determined through a plurality of instances of the processing in a predetermined period as the action of the user in the predetermined period, and in each predetermined period, the transmission controller causes the first communicator to transmit the characteristic information.

In one of the preferred embodiments of the action notification system of the present invention disclosed herein, the electronic device further includes a second body motion sensor that detects body motion of a user, and a second exercise information calculator that calculates exercise information based on a detection signal of the second body motion sensor.

In one of the preferred embodiments of the present invention disclosed herein, an exercise information measurement apparatus includes: a body motion sensor that detects body motion of a user; an exercise information calculator that calculates exercise information based on the detection signal of the body motion sensor; a communicator that communicates with an external apparatus; an action determiner that determines an action of the user based on the detection signal of the body motion sensor; and a transmission controller that causes the communicator to transmit characteristic information of a detection signal waveform of the body motion sensor, which corresponds to the action determined by the action determiner, to an electronic device, wherein the electronic device includes an output device including a vibrator, a speaker, or a light emitter, and an output device controller that causes the output device to operate in accordance with the characteristic information.

In one of the preferred embodiments of the exercise information measurement apparatus of the present invention disclosed herein, the body motion sensor is a triaxial acceleration sensor, the characteristic information includes information indicating an interval between a time at which an amplitude of a portion corresponding to the action in a triaxial composite acceleration waveform, which is the detection signal waveform of the triaxial acceleration sensor, reaches its maximum, and a time at which the amplitude reaches its minimum, and in accordance with the interval, the output device controller determines a period of causing the vibrator to vibrate, a period of causing the speaker to output sound, or a period of causing the light emitter to emit light.

In one of the preferred embodiments of the exercise information measurement apparatus of the present invention disclosed herein, the action determiner periodically performs processing to determine an action of the user based on the detection signal of the body motion sensor, and determine an action that was most often determined through a plurality of instances of the processing in a predetermined period as the action of the user in the predetermined period, and in each predetermined period, the transmission controller causes transmission of the characteristic information to the electronic device.

In one of the preferred embodiments of the present invention disclosed herein, an electronic device includes: a first communicator that communicates with an external apparatus; an output device including a vibrator, a speaker, or the like; a characteristic information acquirer that acquires, via the first communicator, characteristic information of a detection signal waveform of a first body motion sensor, the characteristic information having been transmitted from an exercise information measurement apparatus including a first body motion sensor that detects body motion of a user, a first exercise information calculator that calculates exercise information based on a detection signal of the first body motion sensor, a second communicator that communicates with an external device, an action determiner that determines an action of the user based on the detection signal of the first body motion sensor, and a transmission controller that causes the second communicator to transmit the characteristic information, which corresponds to the action determined by the action determiner; and an output device controller that causes the output device to operate in accordance with the characteristic information acquired by the characteristic information acquirer.

In one of the preferred embodiments of the electronic device of the present invention disclosed herein, the first body motion sensor is a triaxial acceleration sensor, the characteristic information includes information indicating an interval between a time at which an amplitude at a portion corresponding to the action in a triaxial composite acceleration waveform, which is the detection signal waveform of the triaxial acceleration sensor, reaches its maximum, and a time at which the amplitude reaches its minimum, and in accordance with the interval, the output device controller determines a period of causing the vibrator to vibrate, a period of causing the speaker to output sound, or a period of causing the light emitter to emit light.

In one of the preferred embodiments of the electronic device of the present invention disclosed herein further includes: a second body motion sensor that detects body motion of a user; and a second exercise information calculator that calculates exercise information based on the detection signal of the second body motion sensor.

In one of the preferred embodiments of an action notification method of the present invention disclosed herein includes: an action determination step in which an exercise information measurement apparatus including a body motion sensor that detects body motion of a user, an exercise information calculator that calculates exercise information based on a detection signal of the body motion sensor, and a first communicator that communicates with an external device determines an action of the user based on the detection signal of the body motion sensor; a transmission step in which, from the first communicator, the exercise information measurement apparatus transmits characteristic information of a detection signal waveform of the body motion sensor, which corresponds to the action determined in the action determination step; a characteristic information acquisition step in which an electronic device including a second communicator that communicates with an external device and an output device including a vibrator, a speaker, or a light emitter acquires the characteristic information transmitted in the transmission step via the second communicator; and an output device control step in which the electronic device causes the output device to operate in accordance with the characteristic information acquired in the characteristic information acquisition step.

One of the preferred embodiments of a non-transitory computer-readable medium of the present invention disclosed herein includes an action notification program that causes a processor of an exercise information measurement apparatus, which includes a body motion sensor that detects body motion of a user, an exercise information calculator that calculates exercise information based on a detection signal of the body motion sensor, and a first communicator that communicates with an external device, to execute: an action determination step of determining an action of the user based on the detection signal of the body motion sensor; and a transmission control step of causing the first communicator to transmit the exercise information measurement apparatus transmits characteristic information of a detection signal waveform of the body motion sensor, which corresponds to the action determined in the action determination step, to an electronic device, wherein the electronic device includes a second communicator that communicates with an external apparatus, an output device including a vibrator, a speaker, or a light emitting element, a characteristic information acquirer that acquires the characteristic information transmitted in the transmission control step, and an output device controller that causes the output device to operate in accordance with the acquired characteristic information.

In one of the preferred embodiments of the non-transitory computer-readable medium including an action notification program of the present invention disclosed herein, the action notification program causes a processor of an electronic device, which includes a first communicator that communicates with an external device and an output device including a vibrator, a speaker, or a light emitting element, to execute: a characteristic information acquisition step of acquiring, via the first communicator, characteristic information of a detection signal waveform of a first body motion sensor, the characteristic information having been transmitted from an exercise information measurement apparatus including the first body motion sensor that detects body motion of a user, a first exercise information calculator that calculates exercise information based on a detection signal of the first body motion sensor, a second communicator that communicates with an external device, an action determiner that determines an action of the user based on the detection signal of the first body motion sensor, and a transmission controller that causes the second communicator to transmit the characteristic information, which corresponds to the action determined by the action determiner; and an output device control step of causing the output device to operate in accordance with the characteristic information acquired in the characteristic information acquisition step.

According to preferred embodiments of the present invention and modifications thereto, it is possible to provide action notification systems and action notification methods according to which it is possible to deepen a connection between people, and exercise information measurement apparatuses, electronic devices, and non-transitory computer-readable media including action notification programs stored therein that are able to be used in the action notification system.

While the present invention has been described with reference to specific preferred embodiments and modifications thereto, the present invention is not limited to these preferred embodiments and modifications, and many additional modifications can be made without departing from the technical idea of the disclosed invention.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An action notification system comprising:
an exercise information measurement apparatus including a first body motion sensor that detects body motion of a user, a first exercise information calculator that calculates exercise information based on a detection signal of the first body motion sensor, a first communicator that communicates with a first external device, an action determiner that determines an action of the user based on the detection signal of the first body motion sensor, and a transmission controller that causes the first communicator to transmit characteristic information of a detection signal waveform of the first body motion sensor, which corresponds to the action determined by the action determiner; and
an electronic device including a second communicator that communicates with a second external device, an output device including a vibrator, a speaker, or a light emitter, a characteristic information acquirer that acquires the characteristic information transmitted from the exercise information measurement apparatus via the second communicator, and an output device controller that causes the output device to operate in accordance with the characteristic information acquired by the characteristic information acquirer.

2. The action notification system according to claim 1, wherein
the first body motion sensor is a triaxial acceleration sensor;
the characteristic information includes information indicating an interval between a time at which an amplitude of a portion corresponding to the action in a triaxial composite acceleration waveform, which is the detection signal waveform of the triaxial acceleration sensor, reaches a maximum, and a time at which the amplitude reaches a minimum; and
in accordance with the interval, the output device controller determines a period of causing the vibrator to vibrate, a period of causing the speaker to output sound, or a period of causing the light emitter to emit light.

3. The action notification system according to claim 1, wherein
the action determiner periodically performs processing to determine an action of the user based on the detection signal of the first body motion sensor and determines an action that was most often determined through a plurality of instances of the processing in a predetermined period as the action of the user in the predetermined period; and
in each predetermined period, the transmission controller causes the first communicator to transmit the characteristic information.

4. The action notification system according to claim 1, wherein the electronic device further includes a second body motion sensor that detects body motion of a user, and a second exercise information calculator that calculates exercise information based on a detection signal of the second body motion sensor.

5. An exercise information measurement apparatus comprising:
a body motion sensor that detects body motion of a user;
an exercise information calculator that calculates exercise information based on the detection signal of the body motion sensor;
a communicator that communicates with an external apparatus;
an action determiner that determines an action of the user based on the detection signal of the body motion sensor; and
a transmission controller that causes the communicator to transmit characteristic information of a detection signal waveform of the body motion sensor, which corresponds to the action determined by the action determiner, to an electronic device; wherein
the electronic device includes an output device including a vibrator, a speaker, or a light emitter, and an output device controller that causes the output device to operate in accordance with the characteristic information.

6. The exercise information measurement apparatus according to claim 5, wherein
the body motion sensor is a triaxial acceleration sensor;
the characteristic information includes information indicating an interval between a time at which an amplitude of a portion corresponding to the action in a triaxial composite acceleration waveform, which is the detection signal waveform of the triaxial acceleration sensor, reaches a maximum, and a time at which the amplitude reaches a minimum; and in accordance with the interval, the output device controller determines a period of causing the vibrator to vibrate, a period of causing the speaker to output sound, or a period of causing the light emitter to emit light.

7. The exercise information measurement apparatus according to claim 5, wherein
the action determiner periodically performs processing to determine an action of the user based on the detection signal of the body motion sensor, and determines an action that was most often determined through a plurality of instances of the processing in a predetermined period as the action of the user in the predetermined period; and
in each predetermined period, the transmission controller causes transmission of the characteristic information to the electronic device.

8. An electronic device comprising:
a first communicator that communicates with a first external device;
an output device including a vibrator or a speaker;
a characteristic information acquirer that acquires, via the first communicator, characteristic information of a detection signal waveform of a first body motion sensor, the characteristic information having been transmitted from an exercise information measurement apparatus including a first body motion sensor that detects body motion of a user, a first exercise information calculator that calculates exercise information based on a detection signal of the first body motion sensor, a second communicator that communicates with a second external device, an action determiner that determines an action of the user based on the detection signal of the first body motion sensor, and a transmission controller that causes the second communicator to transmit the characteristic information, which corresponds to the action determined by the action determiner; and
an output device controller that causes the output device to operate in accordance with the characteristic information acquired by the characteristic information acquirer.

9. The electronic device according to claim 8, wherein
the first body motion sensor is a triaxial acceleration sensor;
the characteristic information includes information indicating an interval between a time at which an amplitude at a portion corresponding to the action in a triaxial composite acceleration waveform, which is the detection signal waveform of the triaxial acceleration sensor, reaches a maximum, and a time at which the amplitude reaches a minimum; and
in accordance with the interval, the output device controller determines a period of causing the vibrator to vibrate, a period of causing the speaker to output sound, or a period of causing the light emitter to emit light.

10. The electronic device according to claim 8, further comprising:
a second body motion sensor that detects body motion of a user; and
a second exercise information calculator that calculates exercise information based on the detection signal of the second body motion sensor.

11. An action notification method executed by a processor, the method comprising:
determining an action of a user based on a detection signal of a body motion sensor using an exercise information measurement apparatus which includes the body motion sensor that detects body motion of the user and a first communicator that communicates with a first external device;
transmitting, from the first communicator, characteristic information of a detection signal waveform of the body motion sensor, which corresponds to the action determined based on the detection signal of the body motion sensor;
acquiring the characteristic information transmitted from the first communicator via a second communicator using an electronic device including the second communicator that communicates with a second external device, and an output device including a vibrator, a speaker, or a light emitter; and
causing the output device to operate in accordance with the characteristic information acquired via the second communicator.

12. A non-transitory computer-readable medium including an action notification program that causes a processor of an exercise information measurement apparatus, which includes a body motion sensor that detects body motion of a user and outputs a detection signal, and a first communicator that communicates with a first external device, to execute:
determining an action of the user based on the detection signal of the body motion sensor;
causing the first communicator to transmit characteristic information of a detection signal waveform of the body motion sensor, which corresponds to the action determined based on the detection signal of the body motion sensor, to an electronic device;
causing a second communicator of the electronic device to communicate with a second external device;
causing the electronic device to acquire the characteristic information transmitted by the first communicator; and
causing an output device of the electronic device to operate in accordance with the acquired characteristic information, the output device including a vibrator, a speaker, or a light emitting element.

13. A non-transitory computer-readable medium including an action notification program that causes a processor of an electronic device, which has a first communicator that communicates with a first external device and an output device including a vibrator, a speaker, or a light emitting element, to execute:
acquiring, via the first communicator, characteristic information of a detection signal waveform of a body motion sensor, the characteristic information having been transmitted from an exercise information measurement apparatus including the body motion sensor that detects body motion of a user;
determining an action of the user based on the detection signal waveform of the body motion sensor;
causing a second communicator of the exercise information measurement apparatus to communicate with a second external device;
causing the second communicator to transmit the characteristic information, which corresponds to the action of the user determined based on the detection signal waveform of the body motion sensor; and
causing the output device to operate in accordance with the characteristic information acquired via the first communicator.

* * * * *